(12) United States Patent
Vaes et al.

(10) Patent No.: US 9,551,773 B2
(45) Date of Patent: Jan. 24, 2017

(54) ISOLATING ACTIVE ELECTRON SPIN SIGNALS IN EPR

(75) Inventors: Peter Vaes, Bonheiden (BE); Stephanie Teughels, Herent (BE)

(73) Assignee: PEPRIC NV, Leuven (BE)

( * ) Notice: Subject to any disclaimer, the term of this patent is extended or adjusted under 35 U.S.C. 154(b) by 638 days.

(21) Appl. No.: 14/006,153

(22) PCT Filed: Mar. 21, 2012

(86) PCT No.: PCT/EP2012/055042
§ 371 (c)(1),
(2), (4) Date: Sep. 19, 2013

(87) PCT Pub. No.: WO2012/126968
PCT Pub. Date: Sep. 27, 2012

(65) Prior Publication Data
US 2014/0009159 A1 Jan. 9, 2014

(30) Foreign Application Priority Data
Mar. 22, 2011 (GB) .................................. 1104758.6

(51) Int. Cl.
*G01V 3/00* (2006.01)
*G01R 33/60* (2006.01)
*G01N 24/10* (2006.01)
(52) U.S. Cl.
CPC ............... *G01R 33/60* (2013.01); *G01N 24/10* (2013.01)
(58) Field of Classification Search
CPC ....................................................... G01R 33/60
(Continued)

(56) References Cited

U.S. PATENT DOCUMENTS

| 4,604,580 A | 8/1986 | Sugiura et al. |
| 6,504,367 B1 | 1/2003 | Chandrakumar et al. |

(Continued)

FOREIGN PATENT DOCUMENTS

| EP | 2214004 A1 | 8/2010 |
| GB | 2366386 A | 3/2002 |

(Continued)

OTHER PUBLICATIONS

International Search Report from corresponding PCT Application No. PCT/EP2012/055042, Jun. 25, 2012.

(Continued)

*Primary Examiner* — Louis Arana
(74) *Attorney, Agent, or Firm* — Workman Nydegger

(57) ABSTRACT

A system and method involve performing electron paramagnetic resonance on an object under study. The system comprises a first field generator adapted for generating an orienting magnetic field for orienting the magnetization of the object under study and a second field generator adapted for generating RF excitation waves at a frequency to generate electron paramagnetic resonance (EPR) in the object under test. The system also comprises a detection unit adapted for detecting the EPR signals emitted by the object under test and a control unit adapted for controlling the relative orientation of the orienting magnetic field induced by the first field generator with respect to the detection unit. The system furthermore comprises a processing unit programmed for combining detected EPR signals obtained using different relative orientations of the orienting magnetic field with respect to the detection unit.

24 Claims, 5 Drawing Sheets

(58) Field of Classification Search
USPC .................................... 324/316, 319, 322
See application file for complete search history.

(56) References Cited

U.S. PATENT DOCUMENTS

| | | | |
|---|---|---|---|
| 8,816,685 B2* | 8/2014 | Vaes | G01N 24/08 324/312 |
| 2006/0022675 A1 | 2/2006 | Blank et al. | |
| 2014/0210473 A1* | 7/2014 | Campbell | G01N 24/10 324/316 |
| 2014/0285198 A1* | 9/2014 | Halpern | G01R 33/60 324/316 |

FOREIGN PATENT DOCUMENTS

| JP | S5967450 A | 4/1984 |
|---|---|---|
| JP | 59166846 A | 9/1984 |
| JP | H01195354 A | 8/1989 |
| JP | H01198355 A | 8/1989 |
| JP | H0990009 A | 4/1997 |
| JP | 2000065910 A | 3/2000 |
| JP | 2002107316 A | 4/2002 |
| JP | 2005147693 A | 6/2005 |
| JP | 2008151676 A | 7/2008 |

OTHER PUBLICATIONS

Search Report from corresponding GB Application No. 1104758.6, Jul. 5, 2011.

Shirai, Terumitsu, "Low Magnetic Field Measurement with a Reversed-Field Electron-Spin-Resonance Magnetometer", IEEE Transactions on Magnetics, vol. 36, No. 6, Nov. 2000, pp. 3953-3956.

Smirnov, Alex I., et al., "EPR Imaging with Natural Spin Probes", Journal of Magnetic Resonance, Academic Press, Inc., vol. 91, No. 2, Feb. 1, 1991, pp. 386-391.

Database WPI, Week 198533, Thomas Scientific, London, GB, AN 1985-202553, Feb. 7, 1985.

Singh, V., et al., "Temperature and Size Dependence of Electron Magnetic Resonance Spectra of Ni Nanoparticles Embedded in an Amorphous SiO2 Matrix", Journal of Physics Condensed Matter, IOP Publishing, Bristol, GB, vol. 21, No. 45, Nov. 11, 2009, pp. 1-9.

* cited by examiner

ISOLATING ACTIVE ELECTRON SPIN SIGNALS IN EPR

FIELD OF THE INVENTION

The invention relates to the field of electron paramagnetic resonance. More specifically the present invention relates to methods and systems for electron paramagnetic resonance spectroscopy and imaging based thereon.

BACKGROUND OF THE INVENTION

Electron paramagnetic resonance (EPR) allows spectroscopic analysis of substances based on physical concepts analogous to those used in nuclear magnetic resonance (NMR). While NMR allows analysis of substances containing nuclides with non-zero spin, EPR is only applicable to substances containing chemical agents that possess at least one unpaired electron. NMR proves particularly useful in the analysis of substances comprising hydrogen atoms, which are abundantly present in water and hydrocarbons. Furthermore, Magnetic Resonance Imaging (MRI), an imaging technique based on NMR, is a valuable tool in medical diagnosis, due to the subtle contrasts caused by water density and complex spin-spin and spin-lattice interactions in different tissues.

EPR, on the other hand, has found less application in the past because all electrons in most stable chemical compounds are paired. However, the strength of EPR lies in its high specificity. EPR can readily be used for detection and imaging of free radicals in tissues, but the development of specific spin-labeled biological tracer molecules has spawned opportunities for the usage of EPR, and particularly the usage of EPR-based imaging techniques, for analysis of diverse physiological functions in biology and medicine. This opens the way for new tracers, specific to biological mechanisms that can't be studied by conventional means, and for alternatives to tracers used in nuclear medicine, without the implied radiation exposure caused by radionuclides.

EPR typically uses DC magnetic fields of 5 mT to 1.25 T or higher to cause magnetic polarization of particles with non-zero electron spin. Narrow-band radio-frequent waves are used to disturb the magnetization and cause resonance. The frequency at which resonance occurs, referred to as the Larmor precession frequency, is dependent on the applied magnetic field strength and specific material properties, and can range from 200 MHz for low field strengths to 35 GHz or higher for strong fields. The low-field (<30 mT) low-frequency (<1 GHz) region is particularly of interest for applications in biology and medicine because of diminished dielectric loss in tissues.

In Journal of Magnetic Resonance 154 (2002) 287, Yamada, Murugesan et al. compare the two commonly used techniques for EPR spectrometry and imaging, namely Continuous Wave EPR (CW-EPR) and pulsed EPR.

CW-EPR is characterized by the use of prolonged RF excitation wave exposure and a resonant cavity or compound resonator. An impedance match between resonator and RF source allows indirect detection of EPR. When electron resonance occurs, the impedance of the resonator alters, and the EPR signal can be inferred from changes in signal absorption. Typically, magnetic field sweeps in combination with constant frequency RF excitation are used to obtain EPR spectra. CW-EPR may require longer acquisition times and may hence be more susceptible to motion artifacts. Imaging techniques based on CW-EPR offer relatively low resolution and low sensitivity and can exhibit diverse artifacts related to magnetic field modulation, power saturation and motion.

Pulsed EPR, on the other hand, offers higher sensitivity, higher resolution, less artifacts and lower acquisition times. In pulsed EPR, a short, intense RF excitation pulse is used to simultaneously excite spins in a narrow frequency band, followed by detection of the impulse response. The resonator requirements are quite different for pulsed EPR compared to CW-EPR. The resonator for use in pulsed EPR should possess efficient RF power to magnetic field conversion characteristics and a recovery time which is shorter than the response time of the EPR signal. These requirements are mutually conflicting, and limit the suitability of pulsed EPR to signals emitted by paramagnetic particles with narrow linewidths, and therefore long relaxation times, since broad linewidth particles would require an extremely short resonator recovery time. However, many commonly used spin probes, or other feasible spin probes fulfilling the non-zero spin condition, possess broad linewidths.

SUMMARY OF THE INVENTION

It is an object of embodiments of the present invention to provide efficient methods and systems for electron paramagnetic resonance.

It is an advantage of embodiments according to the present invention that the active signal of the electron spins of paramagnetic particles can be isolated from the common mode signal. The common mode signal can comprise contributions from the RF excitation wave, absorption in the object under test and dependencies of the antenna setup on the presence of paramagnetic particles.

It is an advantage of embodiments according to the present invention that methods and systems are provided combining the good detection sensitivity and imaging quality even with the use of broad linewidth spin probes.

It is an advantage of embodiments according to the present invention that the active signal can be isolated from the common mode signal detected while emitting an RF excitation wave.

It is an advantage of embodiments according to the present invention that the active signal of the electron spins of paramagnetic particles possessing broad linewidths and hence short T2 relaxation times, for example magnetic nanoparticles (MNP), can be isolated.

It is an advantage of embodiments according to the present invention that fast and accurate imaging and/or volumetric imaging can be obtained using imaging techniques based on detecting paramagnetic resonance of paramagnetic particles.

It is an advantage of embodiments according to the present invention that the detected signal can be amplified beyond the dynamic range of the measurement device, and that therefore accurate measurements of the active signal can be obtained. It is an advantage of at least some embodiments of the present invention that the latter can be obtained by selectively sampling.

It is an advantage of embodiments according to the present invention that efficient detection can be obtained by using an advantageous configuration of RF field generator and detection unit. It is an advantage of embodiments according to the present invention that a configuration can be used wherein the transmitting antenna and receiving antenna can be maximally isolated, resulting in an improved antenna configuration.

The above objective is accomplished by a method and device according to the present invention.

A system for performing electron paramagnetic resonance on an object under study, the system comprising a first field generator adapted for generating an orienting magnetic field for orienting the magnetization of the object under study and a second field generator adapted for generating RF excitation waves at a frequency to generate electron paramagnetic resonance (EPR) in the object under test, a detection unit adapted for detecting the EPR signals emitted by the object under test, a control unit adapted for controlling the relative orientation of the orienting magnetic field induced by the first field generator with respect to the detection unit so as to be able to detect and combine EPR signals obtained using different relative orientations of the orienting magnetic field with respect to the detection unit.

The system furthermore may comprise a processing unit programmed for combining detected EPR signals obtained using different relative orientations of the orienting magnetic field with respect to the detection unit. It is an advantage of embodiments according to the present invention that in the combined signals the contribution of the active signals of the electron spins of the magnetic particles in the object can be directly detected.

The control unit furthermore may be adapted for controlling the timings of said altering the relative orientation of the orienting magnetic field and the detection unit and of the RF excitations and detection. It is an advantage of embodiments according to the present invention that by detecting for different relative orientations of the orienting magnetic field and the detection unit, the contribution of the surroundings like e.g. the cavity, can be avoided.

The control unit furthermore may be adapted for controlling the relative orientation such that detection can be performed for at least two relative orientations of the orienting magnetic field wherein the orienting magnetic field has a different sign.

The control unit may be adapted for controlling the relative orientation such that detection can be performed for at least two relative orientations of the orienting magnetic field being substantially opposite.

The first field generator may comprise at least one magnet coil connected to a direct current power supply with switchable polarity and wherein the control unit may be adapted for switching the polarity of the current power supply so as to alter the orientation of the magnetic field induced by the at least one magnet coil. It is an advantage of embodiments according to the present invention that an easy implementation of one embodiment of the present invention can be obtained based on a conventional electromagnet, in combination with a control unit.

The system furthermore may comprise a positioning means for altering a relative position between the first field generator and the detection unit for inducing an alteration in the relative orientation of the induced orienting magnetic field and the detection unit. It is an advantage of some embodiments according to the present invention that a difference in relative orientation can be obtained by mechanically rotating the first magnetic field generator or the detection.

The positioning means for altering a relative position may be adapted for rotating the detection unit. Rotating the detection unit may be rotating the ensemble of the detection coil of the detection unit, a coil of the second magnetic field generator and the object.

The positioning means for altering a relative position may be adapted for rotating the first field generator. It is an advantage of embodiments according to the present invention that the first field generator can be rotated as this avoids rotating of more sensitive components.

The control unit may be adapted for providing a continuous variation of the relative orientation of the orienting magnetic field induced by the first field generator with respect to the detection unit during detection of the EPR signals. It is an advantage of embodiments that changing the orienting magnetic field continuously allows increasing the averaging and therefore further increasing the sensitivity of the system. In one embodiment, the orienting magnetic field could be alternatively +10 mT and −10 mT at a certain frequency, such as for example 10 kHz.

The detection unit may comprise a first substantially circular conductive loop and the second field generator may comprise a second substantially circular conductive loop, such that the first and second loop are substantially orthogonal. The isolation between the transmitting and isolating loop should be maximal so that the direct feed through of the exciting signal is minimal. Where in embodiments according to the present invention reference is made to the detection unit and the second field generator being substantially orthogonal, this may include orthogonal as well as slightly deviating from orthogonal for compensating for asymmetries in the antennas used in the detection unit and the second field generator, e.g. because these are not perfect closed loops, and in view of the matching electronics. It is an advantage of embodiments according to the present invention that the configuration of the detection unit and the second field generator can be such that excitation and detection is fully decoupled.

The second field generator may be adapted for generating pulsed RF excitation waves.

The second field generator may be adapted for generating continuous RF excitation waves.

The processing unit may be adapted for combining of measurements of the detected electromagnetic signals obtained using different orientations of the orienting magnetic field in time intervals during which the amplitude of at least one of the signals is smaller than a predetermined threshold. It is an advantage of embodiments according to the present invention that by selectively sampling of the detected electromagnetic signals, the sensitivity of the obtained results can be good, e.g. high or optimized. The amplification may thus be improved beyond the dynamic range of the detection unit.

The system may comprise additional magnetic field gradient generators adapted for imaging and/or volumetric imaging purposes.

The processing unit may be adapted for combining the detected electromagnetic signals in the form of an image and/or volumetric image of the object under test.

The present invention also relates to a method for performing electron paramagnetic resonance, the method comprising applying an orienting magnetic field in an initial orientation with reference to a detection unit to an object under test, exciting the electron spins of paramagnetic particles in the object under test by generating an electromagnetic excitation wave and subsequently detecting electromagnetic signals emitted by the object under test in said detection unit, repeating the excitation and detection step after substantially altering the relative orientation of the orienting magnetic field and the means for detection, and combining detected electromagnetic signals obtained using the different orientations of the orienting magnetic field. Alternatively, the present invention also may relate to a method for performing electron paramagnetic resonance, the method comprising detecting electromagnetic signals emitted by the object under test whereto an orienting magnetic field in an initial orientation with reference to a detection unit has been applied and for which electron spins of paramagnetic particles in the objects were excited by the generation of an electromagnetic excitation wave, repeating detecting electromagnetic signals emitted by the object under test after substantially altering the relative orientation of the orienting magnetic field and the means for detection and after electron spins of paramagnetic particles in the objects were excited by the generation of an electromagnetic excitation wave, and combining the detected electromagnetic signals obtained using the different orientations of the orienting magnetic field.

Said combinings may comprise the combining of measurements of said signals in time intervals during which the amplitude of at least one of the signals is smaller than a predetermined threshold. The amplification may thus be improved beyond the dynamic range of the detection unit.

The excitation and detection steps may be repeated, applying a magnetic field gradient for imaging and/or volumetric imaging purposes in each repetition.

The combining may comprise the generation of an image and/or volumetric image representation of the object under test.

The control unit furthermore may be configured for triggering the processing unit as function of the orienting field.

The present invention also relates to an image or volumetric image obtained by the method as described above.

The present invention also relates to a computer program product for, if implemented on a processing unit, performing the method as described above.

The present invention furthermore relates to a data carrier comprising such a computer program product and to the transmission of such a computer program product over a network.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
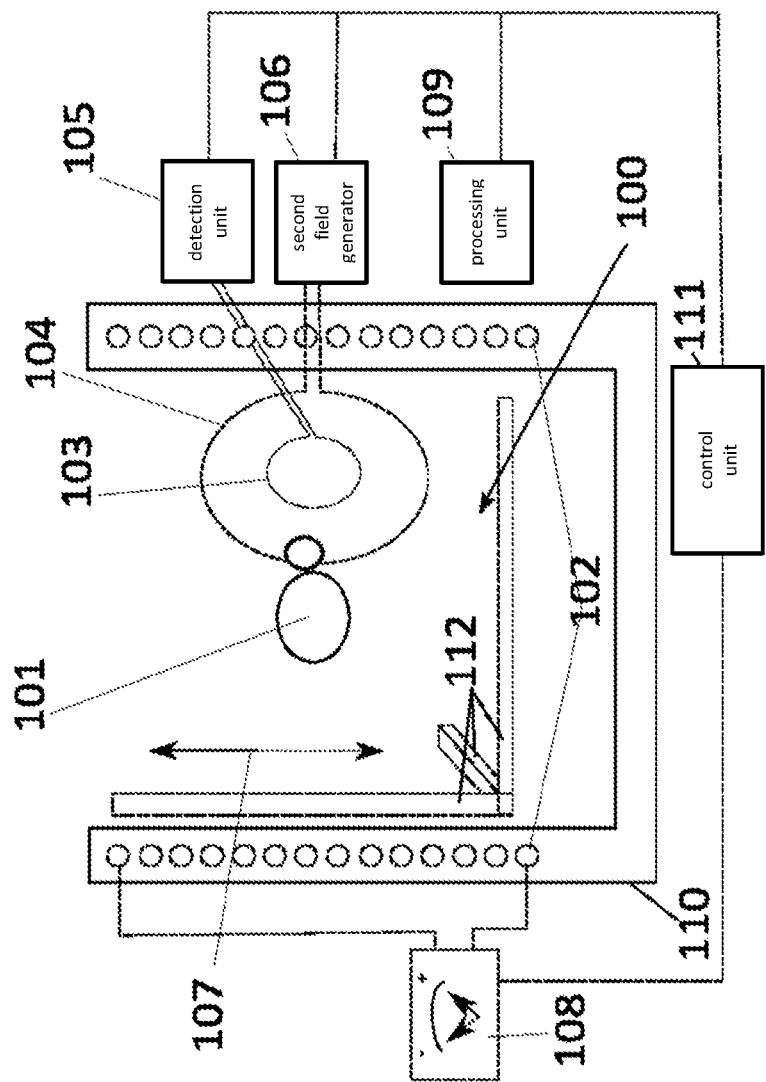
FIG. 1 provides an overview of a system for performing electron paramagnetic resonance subsequently using applied orienting magnetic fields with different orientation, according to an embodiment of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In embodiments of the present invention, methods and system are provided for gathering information about an object under test that includes particles presenting paramagnetic properties. These particles may be introduced in any suitable way such as for example by administering, by mixing, by pouring, etc.

Where in embodiments according to the present invention reference is made to an orienting magnetic field, reference is made to a magnetic field inducing orientation of the magnetization of the particles under study. Such an orienting magnetic field corresponds with the static magnetic field typically used for orienting magnetization of the particles under study in conventional EPR measurements. Nevertheless, as in embodiments of the present invention, the orientation of the magnetic field used for orienting the magnetization of the particles under study is altered for obtaining the full detection signal, in embodiments of the present invention this magnetic field is referred to as orienting magnetic field.

Where in embodiments of the present invention reference is made to RF excitation waves at a frequency to generate electron paramagnetic resonance (EPR) in the object under test, reference is made to RF excitation waves typically having a frequency in the order between 60 and 500 MHz. The excitation wave may be pulsed or continuous wave. The effect of the spins increases with the power of the excitation wave. In pulsed mode more power may be put in the system during the pulses, such as for example up to 200 W.

Where in embodiments of the present invention reference is made to combining of signals, reference is made to mathematical combination of the data representative for the detected EPR signals. Mathematical combination thereby encompasses addition but also any other suitable mathematical processing such as for example determining a linear combination of the data corresponding with the detected EPR signals.

Where in embodiments of the present application the term nano-particles is used, reference is made to particles having a critical dimension, e.g. diameter, in the range of 1 nm to 1000 nm. For a number of embodiments, the size of the particles is further specified to be in a range as provided. The nano-particles or magnetic nano-particles may be single domain particles.

Where in embodiments of the present invention reference is made to magnetic particles with a broad line width, reference may be made to a line width of 3 MHz or larger, e.g. in a range from 3 MHz to 400 MHz. Reference may be made to particles having a line width, e.g. a full width at half maximum FWHM, larger than 5%, e.g. larger than 10%, e.g. larger than 20% of the central line frequency. It is to be noticed that embodiments of the present invention can be advantageously applied to spin systems with a broad line width, although embodiments of the present invention are not limited thereto and can be applied to spin systems with any line width, i.e. including spin systems with narrow line width.

Where in embodiments according to the present invention reference is made to an object under study, such an object may be a non-living object or a living object. In some embodiments—the present invention not being limited thereto—the object may be a body of a living creature, such as for example an animal or human body. The object under study according to embodiments of the present invention are paramagnetic objects. Embodiments of the present invention can also be used for in-vitro testing, e.g. for the quantification of cells linked with the paramagnetic objects). Embodiments of the invention allow to quantify the paramagnetic objects with a high sensitivity and accuracy. Examples of applications include pure quantification to 3D imaging. Objects under study may be paramagnetic objects as of nature or may be made at least partially paramagnetic by adding, e.g. through administering, paramagnetic particles, such as paramagnetic nanoparticles, to the object. The administering step may be performed prior to application of the method according to embodiments of the present invention for detecting electron paramagnetic resonance of the object under study.

Where in method embodiments according to the present invention reference may be made to interaction between an object under study and one or more generated fields, the interaction between object and magnetic field or RF energy may be not part of the method. Method embodiments according to the present invention may thus encompass only the step of detecting upon interaction or the steps of generating the fields and detecting upon interaction.

In a first aspect, the present invention relates to a system for performing electron paramagnetic resonance on an object under study. Embodiments according to the present invention can be used for all types of electron paramagnetic resonance (EPR) detection, such as for example for detecting paramagnetic particles with broad line width—embodiments of the present invention not being limited thereto. According to embodiments of the present invention, the system comprises a first field generator adapted for generating an orienting magnetic field for orienting the magnetization of the object under study and a second field generator adapted for generating RF excitation waves at a frequency to generate electron paramagnetic resonance (EPR) in the object under test. The system furthermore comprises a detection unit adapted for detecting the EPR signals emitted by the object under test and a control unit adapted for controlling the relative orientation of the orienting magnetic field induced by the first field generator with respect to the detection unit. Furthermore, a processing unit programmed for combining detected EPR signals obtained using different relative orientations of the orienting magnetic field with respect to the detection unit is present. By way of illustration, embodiments of the present invention not being limited thereby, standard and optional components of the system for detecting electron paramagnetic resonance will be described in further detail with reference to FIG. 1. In FIG. 1, an exemplary system 100 for performing EPR is depicted. It comprises a first field generator 110 adapted for applying an orienting magnetic field 107 to an object under test 101. Such an orienting magnetic field is an external magnetic field, allowing orientation of the magnetization of the object under study, or paramagnetic particles or portions comprised therein. The first field generator may comprise one or more permanent magnets or one or more electromagnets. Typical magnetic field strengths that may be applied may be in the range 0-50 mT. According to embodiments of the present invention, the relative orientation of the orienting magnetic field with respect to the detection unit, e.g. with respect to the direction of detection, is alterable. In one embodiment of the present invention, this is obtained by the first field generator 110 itself possessing the capability of altering the orientation of the orienting magnetic field 107 (dashed arrow). Said field generator may comprise a magnet coil 102 or a set of magnet coils 102 connected to a power supply 108 with alterable current provision, e.g. switchable polarity. The object under test 101 typically may be placed in a region of sufficient magnetic field homogeneity of the magnetic field induced by the first field generator 110. Such sufficient homogeneity may for example be within a range of 200 ppm or less. The sample position may be in the volume enclosed by the magnet coil 102. Other possibilities for altering the relative orientation may include mechanically displacement of one or more components, as will be illustrated further below.

Furthermore, the system comprises a second field generator 106 adapted for generating radio frequency (RF) excitation waves at a frequency to generate electron paramagnetic resonance (EPR) in the object under test 101. The excitation frequency typically may be in the range between 60 and 500 MHz. The second field generator 106 comprises an antenna (104) which may for example be a coil or a configuration of multiple loops in series or in parallel, may be a helix, etc. Depending on requirements, embodiments may comprise a second field generator 106 adapted for generating continuous RF excitation waves or adapted for generating pulsed RF excitation waves. In other words, continuous wave excitation as well as pulsed excitation can be applied. For both measuring during the excitation pulse is performed. An advantage of pulsed measurements can be that the SAR (Specific Absorption Ratio) can be lowered thus preventing heating of the object, e.g. the body/tissue. For example when measuring alternating positive and negative static fields, RF excitations may only be applied when the static field is set and stable at a certain position. In some embodiments excitation may be excitation using a train of pulses.

The system also comprises a detection unit 105 adapted for detecting EPR signals emitted by the object under test 101 upon excitation. According to embodiments of the present invention, detection may include detection of an echo response induced by the train of pulses. Embodiments of the invention can be used to separate the spin signal from the measured signal when measuring during the exciting pulse, when measuring after the exciting pulse (to measure an echo signal from the spins after an exciting pulse train), or when measuring in CW mode. This applies for all kind of pulse sequences.

The system 100 also comprises a control unit 111 adapted for controlling the relative orientation of the orienting magnetic field 107 induced by the first field generator 110. The control signals provided by the control unit 111 may correspond with driving methods for altering the relative orientation of the orienting magnetic field. One example thereof may be control signals for controlling a DC power supply thus controlling the current through one or more electromagnetic coils of the first field generator and thus controlling the electromagnetic field induced by the first field generator. In one embodiment, current through a single coil is maintained in size but switched in sign, so that an inverse oriented magnetic field is induced. Other examples of control may for example be variation of two orthogonally located coils and providing an altering current through the coils such that a continuous variation in the orientation of the resulting orienting magnetic field is obtained. Still a further example may be the provision of different electromagnetic coils and the subsequent or alternatingly combined provision of current in the different electromagnetic coils such that altering oriented magnetic fields are induced. In other embodiments, the control signals may be adapted for controlling movements of one or more components of the system. The control unit may for example be used for controlling a positioning means for altering a relative position between the first field generator 110 and the detection unit 105. By altering the relative position, again an altered relative orientation of the induced orienting magnetic field and the detection unit can be obtained. In one embodiment, the control unit 111 may be adapted for controlling a position of the detection unit and switch the position of the detection unit with respect to the first field generator. The positioning means may for example be a rotating system rotating the combination of the sample and the antennas of the detection unit 101, 103 and 104 and the second field generator with respect to the first field generator. Another example of an alternative control of the orientation of the orienting field may be a system wherein the control unit is adapted for controlling a positioning means for altering the position of the first field generator 110. The positioning means may for example be a rotating system for rotating the first field generator. The original position of the orienting field is along the z-axis. The first field generator may be rotated so that the field can be rotated around the x- or y-axis or a combination of both.

Said embodiments may additionally comprise a control unit 111 adapted for controlling the timings of said polarity reversals, RF excitations, EPR detections and/or combinings. The system 100 also comprises a processing unit 109 for combining detected signals obtained using the different orientations of the polarizing magnetic field 107. The processing unit 109 in embodiments according to present invention may be adapted for adding or subtraction of measurements or providing other combinations, e.g. linear combinations, of the detected signals obtained using different orientations of the polarizing magnetic field 107.

By way of illustration, embodiments of the present invention not being limited thereby, a number of examples of measurements using different orientation of the orienting magnetic field with reference to the orientation of the detection unit are discussed below.

In a first example, in essence two measurements are combined whereby during a first measurement the orienting magnetic field is according to a first direction and in a second measurement the orienting magnetic field is in the opposite direction but having the same magnitude. In other words, between the two measurements, the sign of the orienting magnetic field is altered. Such reverse orientation can e.g. be obtained using an electromagnetic coil wherein the current is reversed in direction while maintained in amount, by rotating a permanent magnetic field as first field generator over 180° or by rotating the detection unit over 180°.

By way of illustration, embodiments of the present invention not being limited thereto, features and advantages of at least some embodiments of the present invention can be understood from following mathematical considerations. It is to be understood that nor the mathematical formalism used, nor any approximation used or contribution not taken into account may be considered limiting for embodiments of the present invention.

Assuming the measured data are indicated by the operator $V_{out}(\theta)$ with $\theta$ being the angle of the orienting magnetic field, the operator feedthrough($\theta$) represents the contribution of the exciting signal to the measured data and the operator effect($\theta$) represents the contribution of the spins. The effect of using opposing orienting magnetic fields is shown below: For opposite orienting magnetic fields, the two measurement results are shown below:

$$V_{out}(0°) = \text{feedthrough } (0°) + \text{effect } (0°) + \text{noise } 1$$

$$V_{out}(180°) = \text{feedthrough } (180°) + \text{effect } (180°) + \text{noise } 2$$
$$= \text{feedthrough } (0°) - \text{effect } (0°) - \text{noise } 2$$

The combined effect thus results in:

$$V_{out}(0°) - V_{out}(180°) = 2 \times \text{effect}(0°) + \text{noise1} - \text{noise2}$$

As can be seen, the contribution of the exciting signal to the measured data is filtered out and the noise can be reduced. The reduction of noise that can be obtained is illustrated by the following considerations: The sensitivity can be improved by increasing the frequency of the orienting field, resulting in noise reduction. Assuming the measured data are indicated by the operator $V_{out}(f)$, where f is the size of the orienting field and whereby the field is oriented along the z-axis. The effect can be isolated—in a similar manner as described above—by subtracting the measurements of two opposite fields:

$$V_{out}(f) - V_{out}(-f) = 2 \cdot \text{effect}(f) + \text{noise1} - \text{noise2}.$$

For the actual measurements in the present example the size of the orienting field f equals 10 mT. The field is applied using Helmholtz coils around the setup. The current through the coils is changed sinusoidal generating a field with as maximum 10 mT and as minimum −10 mT. Each time the maximum or minimum is reached the start of a new measurement is triggered. The noise can then be reduced by averaging a lot of measurements $$\sum_1^n V_{out}(f) - V_{out}(-f)$$

The averaging is done real-time in a processor, in the present example using a FPGA, and is triggered by the field trigger at ±10 mT.

By reducing the time between measurements it was shown experimentally that the noise can be reduced. For the same amount of averaging and using the same setup the noise level for a background measurement is as shown in the table below, illustrating that the noise level is reduced for higher frequencies.

| Measurement frequency (Hz) | Noise level (mV) |
|---|---|
| 1 | 0.05 |
| 100 | 0.005 |
| 200 | 0.002 |

This means a sensitivity improvement with a factor 25 between measurement at 1 Hz measurement at 200 Hz. As indicated here above, by real-time processing of the incoming data, e.g. using an fpga triggered be the orienting field trigger, the noise can be reduced using the following processing $$\sum_1^n V_{out}(f) - V_{out}(-f)$$

Whereby extracting the effect from the measured data can be accurately performed, thereby decreasing the noise by increasing n.

To account for changes in the feedthrough signal additionally the following processing also can be done $$\sum_1^n V_{out}(f) + V_{out}(-f).$$

Figure 7:
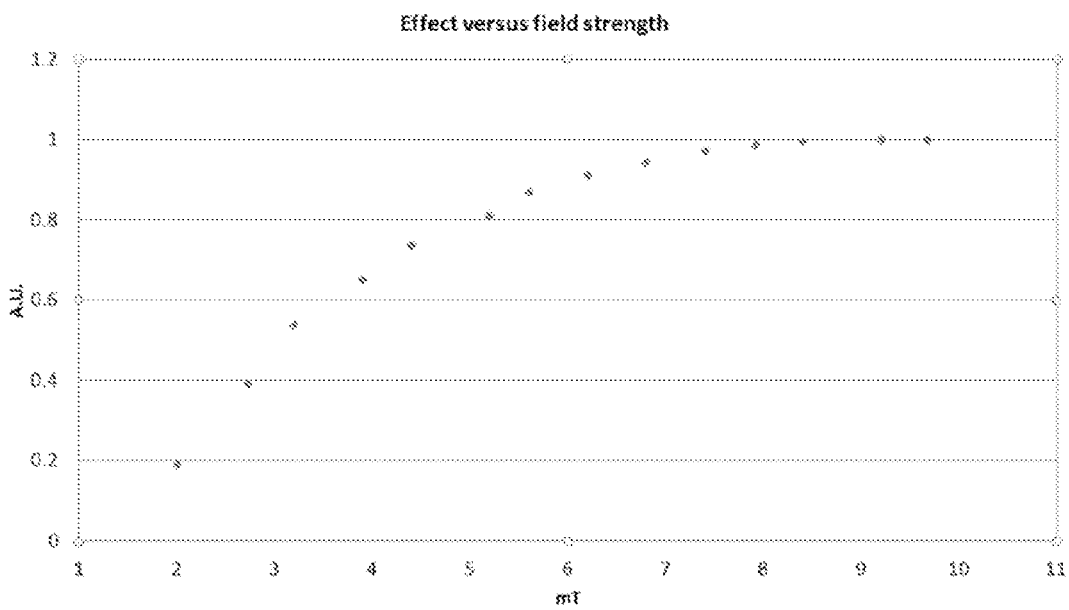
FIG. 7 illustrates the measured effect as function of the field strength using a method according to an embodiment of the present invention.

By way of illustration, FIG. 7 illustrates the effect of field strength on the effect that can be measured during sinusoidal modification of the orienting field along the z-axis. For 14 field strengths, $V_{out}(f)$ is measured and processed by the FPGA. The effect that can be measured is illustrated as function of the field strength.

In still another example, measurements are performed continuously while rotating the orienting magnetic field continuously. In this way integration of the detected signals result in detection results for substantially all orientations of the orienting magnetic field, such that contributions of neighbouring effects are removed. The measurement speed can be increased by measuring continuously for the different applied static fields. When rotating the static field at a certain speed, the measured effect will change with the same frequency. Noise can be reduced by specifically looking for an effect varying with that frequency, bandpass filtering around this frequency is a possibility. The varying orientation of the orienting magnetic field may be obtained by continuously rotating the first field generator around the detection unit, by continuously rotating the detection unit around the first field generator or by continuously varying the orientation of the field generated by the first field generator, e.g. using two orthogonally positioned coils or a combination of orthogonally positioned Helmholtz coils wherein the current is varied, such that the combined effect is a continuously varying orienting magnetic field.

In yet another example, a combination is made of three different relative orientations, each spaced over an angle of 120°. Obtaining a linear combination of the detected results obtained for these different relative orientation also allows to filter out the neighbouring effects from the actual spin contributions. Orienting magnetic fields in such three orientations may for example be obtained using different coils or by rotating permanent magnets with respect to the detection unit or rotating the detection unit with respect to the first field generator.

In order to estimate the contribution measured, it is to be noticed that only the projection of the magnetization on the z-axis which will be tilted by the exciting RF pulse. If the orienting magnetic field is not along the z-axis, the projection of the magnetization will therefore be smaller. After tilting the magnetization, the projection on the y-axis will be a measure for the size of the effect measured by the receive antenna. The tilting angle itself depends on the particle properties, e.g. the relaxation times T1, T2 and the ratio of both may play a significant role.

It is to be noticed that particular orientations of the orienting magnetic field as well as the optimal combination of the corresponding detection results can be selected, e.g. based on calculation or trial and error or benchmarking of known samples.

Further by way of illustration, embodiments of the present invention not being limited thereto, a number of particular embodiments will further be described below.

One particular embodiment describes a system as discussed above, wherein the second field generator 106 and the detection unit 105 each comprise a substantially circular conductive loop 103, 104. The conductive loop thereby are such that one loop fits into the other loop. In such a configuration the conductive loop 104, acting as transmission antenna, can be shielded from the conductive loop 103, acting as detection antenna. Increasing the transmission/detection isolation results in a smaller detected total signal and therefore in a larger effect to signal ratio. Such antenna configurations may consist but are not limited to two circular loops. Different geometrical configurations may be possible: helix structure, single loops, multiple loops, in series, in parallel, concentric with different diameters. In all antenna configuration an important parameter is the isolation between the transmitting and receiving antenna.

In a particular example, the data used for combining detection results are selected such that a high or even optimal object spin contribution is obtained. This can be done either by detecting only during those time intervals that separation between the spin contribution and neighbouring effects is optimal or by using only those parts of detected data corresponding therewith. In a particular embodiment, combination of detected signals or data corresponding therewith may be a combination of data detected in selected time intervals during which the amplitude of at least one if the signals is smaller than a predetermined threshold. In other words, sampling can be done where the effective object spin contributions are high or optimal.

Embodiments of present invention may comprise additional magnetic field gradient generators 112 adapted for imaging and/or volumetric imaging purposes. Such embodiments may furthermore comprise a procession unit 109 adapted for combining the detected signals in the form of image and/or volumetric image representations of the object under test 101. By way of illustration, embodiments of the present invention not being limited thereby, in one example imaging could be performed by inducing a field gradient over the sample. For example in a 1-dimensional case, applying a field gradient (e.g. 0→10 mT) over the sample (e.g field of view of 2 cm), the spins will give a different response depending on their position (corresponding with the Langevin equation). Applying different field gradients (e.g. 0→5 mT, 10→0 mT, . . . , 0→−10 mT, −10→0 mT, 0→−5 mT) will result in a set of equations allowing resolving the concentrations at each of the individual positions. The latter can be extended to 2 or 3 dimensions. In another example, resonance condition is created only at one position. +/−10 mT at one location and 0 mT at all the other locations.

Figure 2:
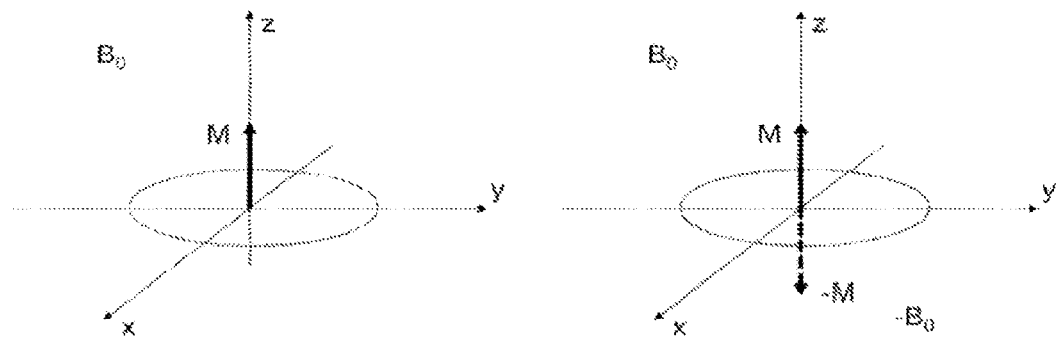
FIG. 2 illustrates the magnetization of electron spins as function of different orientations of the applied orienting magnetic fields, as used in embodiments according to the present invention.

Without wishing to be bound by theory, the principles of embodiments according to the present invention can be explained with reference to FIG. 2 and FIG. 3, indicating the magnetization M of the spin system induced by an external magnetic field $B_0$. By way of illustration, embodiments of the present invention not being limited thereto, principles according to embodiments of the present invention will be illustrated using orienting magnetic fields being equal in magnitude but opposite in sign. It is to be noticed that various alternatively orientations of the orienting magnetic fields also may be applied. The left drawing of FIG. 2 shows the magnetization of the spin system in a conventional EPR setup when subjected to a magnetic field $B_0$ parallel to the vertical axis z. In the right drawing of FIG. 2 the same situation is depicted for the EPR setup in present invention. While the same magnetization M is induced by a magnetic field $B_0$ as in the conventional setup, it will be seen that the magnetization is inverted (−M, dashed line) when subjected to the inversed magnetic field $-B_0$.

Figure 3:
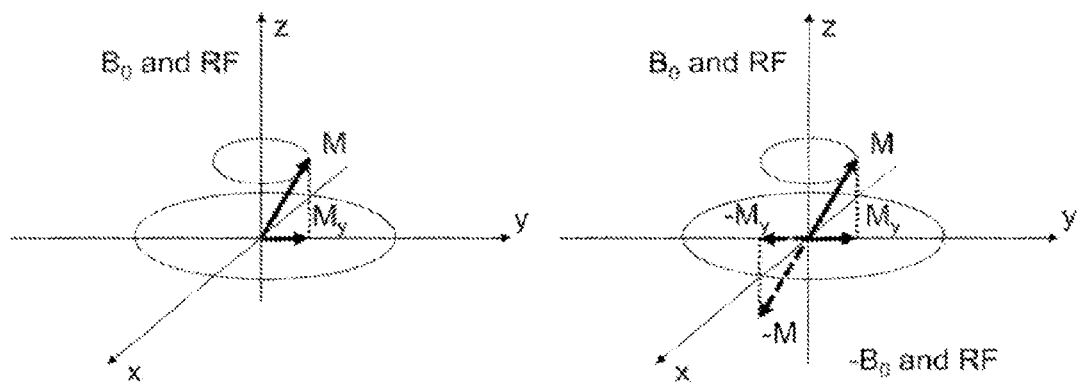
FIG. 3 illustrates the magnetization of electron spins as influenced by orienting magnetic fields at different orientation in combination with an RF excitation wave, as used in embodiments according to the present invention.

When an RF wave satisfying the Larmor resonance criterion is applied to the spin system magnetized by the magnetic field $B_0$, the magnetization will be perturbed as shown in the left drawing of FIG. 3, which results in a precessing motion around the z-axis at the Larmor resonance frequency. When the same RF wave is applied to the spin system magnetized by the inverted magnetic field $-B_0$, a processing motion occurs at the same frequency but with an 180° phase shift, as indicated by the inverted vector −M (dashed) in the right drawing of FIG. 3.

An example of how the different components can be present with respect to FIG. 3 may be the sample being in the centre, the receiving antenna being substantially in the x-z plane for detecting the $M_y$ component, the exciting antenna is substantially in the y-z plane for tilting the spins and the transmitting antenna being around the receiving antenna. In the present example, the centre of the antennas is in the center of the coordinate system and the isolation between the receiving and the transmitting antenna is thus maximized.

Figure 4:
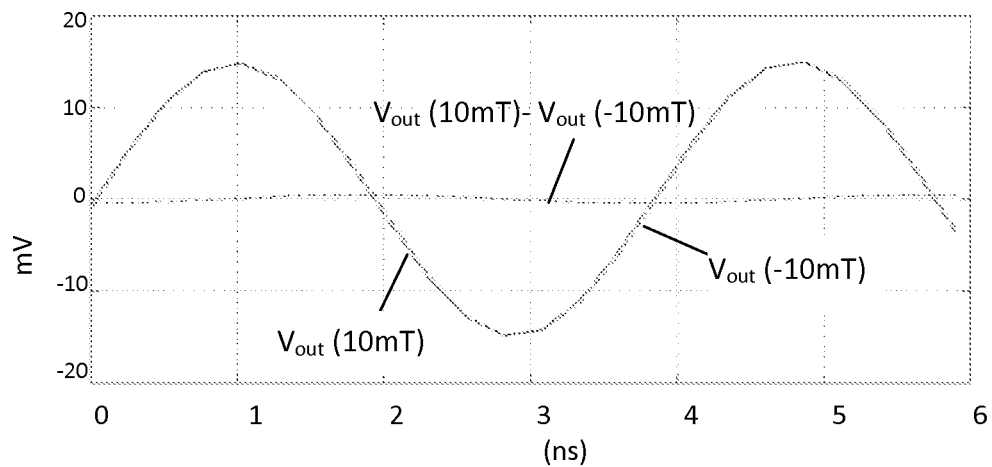
FIG. 4 illustrates the obtained measurement signals for applied orienting magnetic fields with opposite orientation as well as the combined measurement signal indicating the spin contribution, as can be obtained using embodiments according to the present invention.

A receiving antenna will detect an EPR signal proportional to a projection $M_y$ of the precessing magnetization vector M. Measuring the RF signal twice, once applying the initial magnetic field $B_0$ and once applying the inverted magnetic field $-B_0$, and both after application of the same RF excitation wave, allows separation of the EPR signal of the spin system, referred to as the active signal, by subtraction of the common mode detected signals, which may be affected by absorption effects, effects dependent on antenna setup, the RF excitation wave directly and resonations other than the electron spin resonances under study. This is illustrated in the graph in FIG. 4, where the active signal amplitude in mV (dashed-dotted line) obtained by subtraction of both common mode signal amplitudes (full line and dotted line) is shown in function of time.

Figure 5:
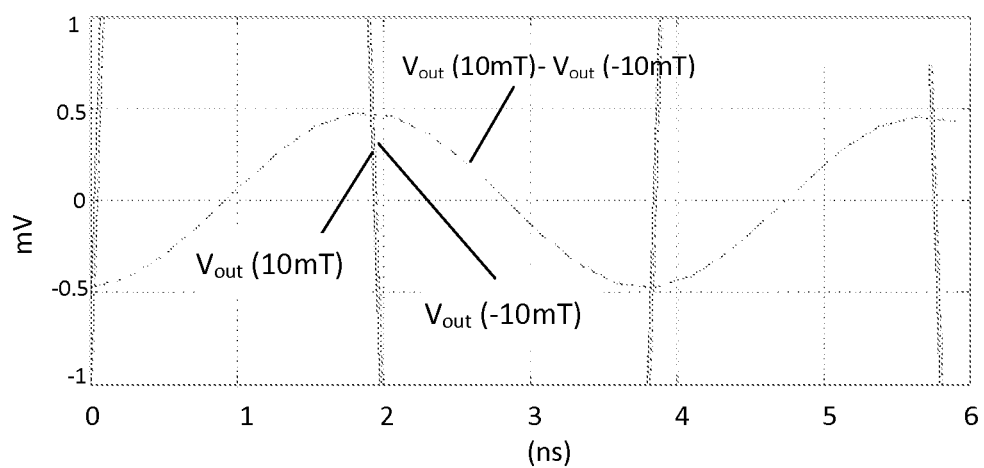
FIG. 5 illustrates the electron spin contribution in the processed signal based on measurements under influence of orienting magnetic fields with opposite orientation, as can be obtained using embodiments according to the present invention.

In FIG. 5, the same data are shown on a smaller signal amplitude scale. The phase shift between the active signal and the common mode signals is about 90°, as evidenced by the proximity of the extrema of the active signal amplitude to the zero-crossings of the common mode signals. This allows estimation of the active signal by extrapolation of subtracted measurements of the common mode signals near the active signal extrema, i.e. sampled in intervals where the absolute value of the common mode signal amplitudes are below a predetermined threshold. This is particularly appealing because the dynamic range of the sampling process can be limited to a fraction of the amplified common mode signal range, and therefore the measurement precision and lower limit of detection can be increased. As it has been noticed that the maximum is not always reached exactly at 90° but rather around 90°, the sampling may be adapted such that the optimum sampling moment is determined e.g. using an algorithm which modifies the sample moment, calculates the effect, and modifies the sample moment until the maximum effect is reached.

It should be noted that due to the dependence of the antenna setup on the static field, a remaining signal, not caused by the spin system, will be present after subtracting a measured signal in the absence of the magnetic field $B_0$ from a signal measured in the presence of the magnetic field $B_0$. Therefore, the systems and methods of present invention offer signal separation superior to normalization at zero Gauss. Additionally, the active signal contributes equally to both total signal measurements, for positive and negative orientation of $B_0$, resulting in a doubling of the measured effect.

Figure 6:
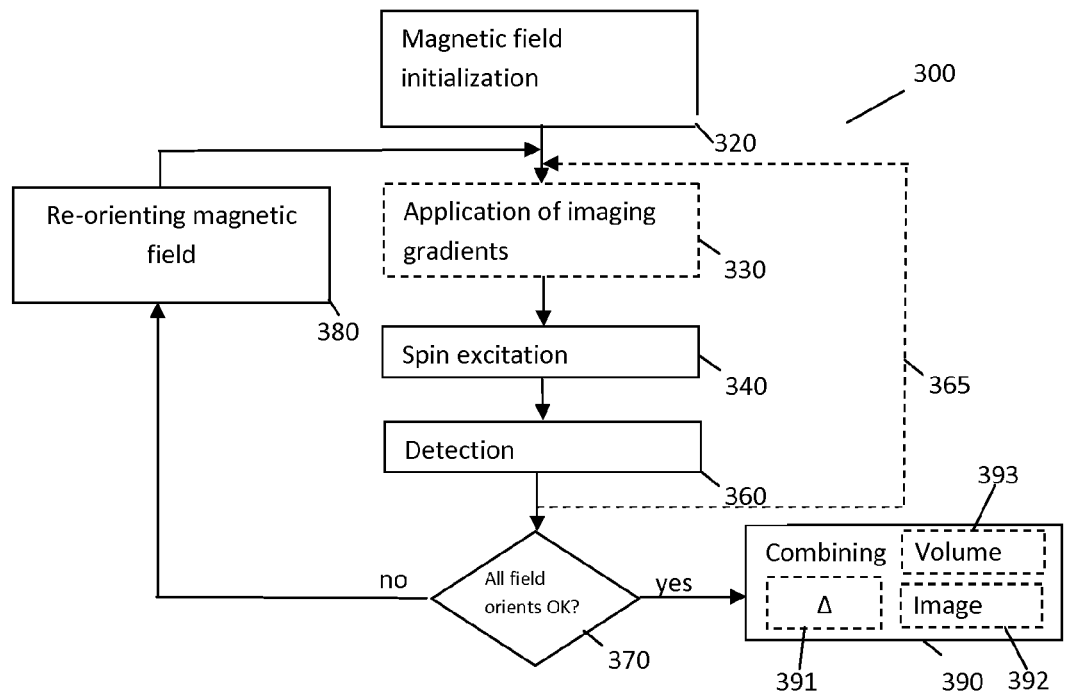
FIG. 6 illustrates an exemplary method for performing electron paramagnetic resonance characterization using orienting magnetic fields with different orientation, according to an embodiments of the present invention.

In a second aspect, embodiments of the present invention relate to a method of performing electron paramagnetic resonance. The method comprises applying to an object under test an orienting magnetic field in an initial orientation with reference to a detection unit, exciting the electron spins of paramagnetic particles or portions in the object under test by generating an RF electromagnetic excitation wave and subsequently detecting in said detection unit a response electromagnetic signal emitted by the object under test. The method further comprises repeating the excitation and detection step after substantially altering the relative orientation of the orienting magnetic field and the means for detection. The method also comprises combining detected electromagnetic signals obtained using the different orientations of the orienting magnetic field. The method may advantageously be performed using a system as described in the first aspect, although embodiments of the present invention are not limited thereto. By way of illustration, embodiments of the present invention not being limited thereto, an example of a method is shown in the flow diagram in FIG. 6, illustrating standard and optional steps for the method.

The method comprises the steps of applying 320 a polarizing magnetic field in an initial orientation to an object under test, for instance a magnetic field of less than 1.25 T, with sufficient homogeneity of strength and orientation over the volume of the object, e.g. 200 ppm or less, exciting 340 the electron spins of paramagnetic particles, for instance magnetic nanoparticles (HNPs), in the object under test by generating an electromagnetic excitation wave, for instance an RF wave of frequency less than 35 GHz, typically a RF wave of frequency about equal to the Larmor resonance frequency dictated by the strength of the applied magnetic field.

The method comprises in step 360, detecting electromagnetic response signals emitted by the object under test.

The method furthermore comprises subsequently repeating 370 the excitation 340 and detection 360 step after substantially altering, e.g. inverting, 380 the relative orientation of the polarizing magnetic field and the means of excitation and detection. Such a step may be repeated for a plurality of different orientations. In addition thereto, such a repeating step may be performed for a plurality of times for the same orientation and for different orientations in order to improve detection statistics.

The method further comprises, e.g. after the detection response signals for the different orientations one intends to use are obtained, combining 390 the detected electromagnetic signals obtained using different orientations of the orienting magnetic field. Such a combining step also may be performed at least partially during use, e.g. by integrating the results during altering orientations of the orienting magnetic field.

In certain embodiments of the present invention, such combinings 390 may comprise the subtraction additions or other linear combinations of measurements or data corresponding therewith, obtained in time intervals during which the amplitude of at least one of the signals is smaller than a predetermined threshold.

In certain embodiments of the present invention, the applied method furthermore comprises iterations 365 of applying 330 magnetic field gradients for imaging purposes, exciting 340 the electron spins and detecting 360. The gradients in 330 can be selected in such way that the magnetic field strength in a predetermined volume of space meets the electron resonance requirements of the excitation wave in 340. The number of iteration steps 365 may be defined by a predetermined scan range, scan resolution and spatial scanning strategy, such that an image and/or volumetric image representation of the object can be generated 392 in the combining step 390 by analyzing emitted signals obtained in the iteration steps 365 using different field gradients 330, each selecting a different EPR sensitive volume of space.

In such embodiments the excitation wave in 340 may furthermore be adapted to detect a phase-encoded signal in 360 from which additional spatial information can be obtained in the combining step 390.

Other features and optional steps may correspond with the functionality of components described with reference to systems for performing electron paramagnetic resonance, as described in the first aspect.

In one aspect, embodiments of the present invention also relate to computer-implemented methods for performing at least part of the methods as described above or to corresponding computing program products. Such methods may be implemented in a computing system, such as for example a general purpose computer. The computing system may comprise an input means for receiving data. The system may be or comprise a data processor for processing data, e.g. the electron paramagnetic resonance data of the single domain particles. The computing system may include a processor, a memory system including for example ROM or RAM, an output system such as for example a CD-rom or DVD drive or means for outputting information over a network. Conventional computer components such as for example a keyboard, display, pointing device, input and output ports, etc also may be included. Data transport may be provided based on data busses. The memory of the computing system may comprise a set of instructions, which, when implemented on the computing system, result in implementation of part or all of the standard steps of the methods as set out above and optionally of the optional steps as set out above. Therefore, a computing system including instructions for implementing part or all of a method as described above is not part of the prior art.

Further aspect of embodiments of the present invention encompass computer program products embodied in a carrier medium carrying machine readable code for execution on a computing device, the computer program products as such as well as the data carrier such as dvd or cd-rom or memory device. Aspects of embodiments furthermore encompass the transmitting of a computer program product over a network, such as for example a local network or a wide area network, as well as the transmission signals corresponding therewith.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention.

By way of illustration, embodiments of the present invention not being limited thereto, two examples of applications are discussed in more detail below.

In a first example, a method and/or system according to embodiments of the present invention is used for screening a sample for identifying a concentration distribution in a sample. This application makes use of the fact that in the typical orthogonal antenna setup of embodiments of the present invention, the volume in which the RF signal is high is limited. As the response of the electron spins is thus depending on the position of the spins within the antennas, a certain distribution of the electron spins over a length of the sample (i.e. a longitudinal distribution) can be determined.

By moving the sample in discrete steps over the longitudinal direction through the antennas (e.g. shifting each time over a distance of 1 mm or alike) and by measuring for each position of the sample the measurement response, the necessary information—in combination with the response function for electron spins to an antenna field—can be obtained for determining information regarding the longitudinal distribution of the electron spins in the sample.

Figure 8:
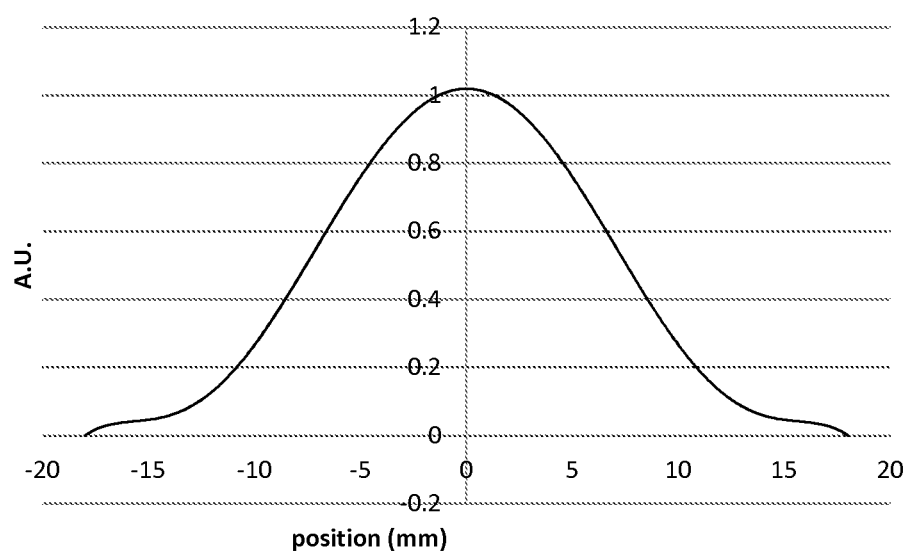
FIG. 8 illustrates an example of the spin response of electron spins of a sample in an antenna setup according to an embodiment of the present invention, whereby the response is illustrated as function of the distance to the centre point of the antenna setup.

A typical response function (f(x)) of electron spins to a particular antenna configuration can be established for each antenna configuration. Such a typical response function expresses the response of electron spins as function of their position with respect to the antenna configuration is shown by way of example in FIG. 8. The position with respect to the center of the antenna configuration is indicated as follows: Position 0 mm means that the electron spins are in the centre of the antennas, other positions indicate the distance from the electron spins to the centre of the antennas.

In practice, screening of a longitudinal concentration distribution can for example be performed by solving the set of linear equations to be solved for the spin distribution, each equation representing a measurement for a different position of the sample with respect to the antenna setup. Given the spin response function f(x) whereby x expresses the position and given an unknown certain spin distribution (C1, ... Cn), one can derive the set of linear equations with the unknown concentration profile being C1 on position −p, ... C2 on position—p+1, ... Cn on position −p+n−1 as follows:

In a first measurement for a first position of the sample with respect to the antennas a first measurement result M1 is obtained, which can be expressed as:

$$f(-p)*C1+f(-p+1)*C2+ \ldots +f(-p+n-1)*Cn=M1$$

Moving the sample to a second position with respect to the antennas (e.g. moving in longitudinal direction over a distance of 1 unit (e.g. 1 mm)) results in the following equation:

$$f(-p+1)*C1+f(-p+1+1)*C2+ \ldots + f(-p+1+n-1)*Cn=M2$$

Moving the sample over m+1 distance units in longitudinal direction (e.g. over m+1 millimeter) results in the following equation:

$$f(-p+m+1)*C1+f(-p+m+1+1)*C2+ \ldots +f(-p+m+1+n-1)*Cn=Mm$$

Combining the above equations, results in the following set of equations $$\begin{bmatrix} f(-p) & f(-p+1) & \ldots & f(-p+n-1) \\ f(-p+1) & f(-p+2) & \ldots & f(-p+n) \\ \vdots & \vdots & \ldots & \vdots \\ f(-p+m+1) & f(-p+m+2) & \ldots & f(-p+m+n) \end{bmatrix} * \begin{bmatrix} C1 \\ C2 \\ \vdots \\ Cn \end{bmatrix} = \begin{bmatrix} M1 \\ M2 \\ \vdots \\ Mm \end{bmatrix}$$

Since f, the spin response as function of the position, is known (measured) for a specific antenna set and since the measurement responses M1, ... Mm are measured for each position for the sample, a set of linear equations which can be solved for C1, ... Cn is obtained. In this way, a concentration profile can be determined.

In a second application, imaging of a sample is obtained, whereby for imaging, the size (or direction) of the orienting magnet field over the sample is varied. This will make the response of the electron spins position dependent as the measured effect is depending on the field strength, as shown in FIG. 7. By changing the spatial distribution of the orienting field and each time measuring the response a set of linear equations can be obtained which can be solved for the concentration distribution of the electron spins (and therefore also for the concentration distribution of the particles). By expressing the concentration of particles (e.g. by attributing an intensity corresponding with the concentration) as function of their position in the sample, pixel information (intensity, location) is obtained, whereby a full set of pixels can build a full image of the sample, more particularly a concentration distribution image for the sample.

The above applications illustrate advantageous features of embodiments of the present invention.

The invention claimed is:

1. A system for performing electron paramagnetic resonance on an object under study, the system comprising
   a first field generator adapted for generating an orienting magnetic field for orienting the magnetization of the object under study and
   a second field generator adapted for generating RF excitation waves at a frequency to generate electron paramagnetic resonance (EPR) in the object under test,
   a detection unit adapted for detecting the EPR signals emitted by the object under test,
   a control unit adapted for controlling and altering the relative orientation of the orienting magnetic field induced by the first field generator with respect to the detection unit, wherein the control unit is adapted for controlling the timing of said altering of the relative orientation and of the RF excitations and detection so as to be able to detect and combine EPR signals obtained using different relative orientations of the orienting magnetic field with respect to the detection unit, and the system furthermore comprises a processing unit programmed for combining detected EPR signals obtained using different relative orientations of the orienting magnetic field with respect to the detection unit so as to filter out the contribution of the exciting signal to the measured data.

2. The system according to claim 1, wherein the control unit is adapted for controlling the relative orientation such that detection can be performed for at least two relative orientations of the orienting magnetic field wherein the orienting magnetic field has a different sign.

3. The system according to claim 1, wherein the control unit is adapted for controlling the relative orientation such that detection can be performed for at least two relative orientations of the orienting magnetic field being substantially opposite.

4. The system according to claim 1, wherein the first field generator comprises at least one magnet coil connected to a direct current power supply with switchable polarity and wherein the control unit is adapted for switching the polarity of the current power supply so as to alter the orientation of the magnetic field induced by the at least one magnet coil.

5. The system according to claim 1, further comprising a positioning unit configured to alter a relative position between the first field generator and the detection unit for inducing an alteration in the relative orientation of the induced orienting magnetic field and the detection unit.

6. The system according to claim 5, wherein the positioning unit configured to alter a relative position is adapted for rotating the detection unit.

7. The system according to claim 5, wherein the positioning unit configured to alter a relative position is adapted for rotating the first field generator.

8. The system according to claim 5, wherein the control unit is adapted for providing a continuous variation of the relative orientation of the orienting magnetic field induced by the first field generator with respect to the detection unit during detection of the EPR signals.

9. The system according to claim 1, wherein the detection unit comprises a first substantially circular conductive loop and the second field generator comprises a second substantially circular conductive loop, such that the first and second loop are substantially orthogonal.

10. The system according to claim 1, wherein the second field generator is adapted for generating pulsed RF excitation waves.

11. The system according to claim 1, wherein the second field generator is adapted for generating continuous RF excitation waves.

12. The system according to claim 1, wherein the processing unit is adapted for combining of measurements of the detected electromagnetic signals obtained using different orientations of the orienting magnetic field in time intervals during which the amplitude of at least one of the signals is smaller than a predetermined threshold.

13. The system according to claim 12, wherein the system is adapted for obtaining measurements of the detected electromagnetic signals obtained using different orientations of the orienting magnetic field in time intervals during which the amplitude of at least one of the signals is smaller than a predetermined threshold such that an amplification of the detected signals are obtained beyond the dynamic range of the detection unit.

14. The system according to claim 1, wherein the system comprises additional magnetic field gradient generators adapted for imaging and/or volumetric imaging purposes.

15. The system according to claim 1, wherein the processing unit is adapted for combining the detected electromagnetic signals in the form of an image and/or volumetric image of the object under test.

16. The system according to claim 1, wherein the control unit is configured for triggering the processing unit as function of the orienting field.

17. A method for performing electron paramagnetic resonance, the method comprising:
   applying an orienting magnetic field in an initial orientation with reference to a detection unit to an object under test,
   exciting the electron spins of paramagnetic particles in the object under test by generating an electromagnetic excitation wave and subsequently detecting electromagnetic signals emitted by the object under test in said detection unit,
   repeating the excitation and detection step after substantially altering the relative orientation of the orienting magnetic field and the detection unit,
   wherein the method further comprises
   controlling the timing of the altering of the relative orientation, the exciting and the detecting used for the different relative orientation, and
   combining detected electromagnetic signals obtained using the different orientations of the orienting magnetic field so as to filter out the contribution of the exciting signal to the measured data.

18. The method according to claim 17, wherein said step of combining comprise the combining of measurements of said signals in time intervals during which the amplitude of at least one of the signals is smaller than a predetermined threshold.

19. The method according to claim 18, wherein the sampling results in amplification beyond the dynamic range of the detection unit.

20. The method according claim 17, wherein the excitation and detection steps are repeated, applying a magnetic field gradient for imaging and/or volumetric imaging purposes in each repetition.

21. The method according to claim 20, wherein said step of combining comprise the generation of an image and/or volumetric image representation of the object under test.

22. A non-transitory computer-readable medium having instructions stored thereon, which, when implemented on one of more processing units, cause the one or more processing units to perform a method for performing electron paramagnetic resonance, the method comprising
   applying an orienting magnetic field in an initial orientation with reference to a detection unit to an object under test,
   exciting the electron spins of paramagnetic particles in the object under test by generating an electromagnetic excitation wave and subsequently detecting electromagnetic signals emitted by the object under test in said detection unit,
   repeating the excitation and detection step after substantially altering the relative orientation of the orienting magnetic field and the detection unit wherein the method further comprises
controlling the timing of the altering of the relative orientation, the exciting and the detecting used for the different relative orientation, and
combining detected electromagnetic signals obtained using the different orientations of the orienting magnetic field so as to filter out the contribution of the exciting signal to the measured data.

23. A data carrier comprising the non-transitory computer-readable medium according to claim 22.

24. A method comprising the step of transmitting the instructions stored on the computer-readable medium according to claim 22 over a network, which, when implemented on one or more processing units, cause the one or more processing units to perform the method for performing electron paramagnetic resonance.

\* \* \* \* \*